(12) United States Patent
Timken et al.

(10) Patent No.: US 10,167,432 B2
(45) Date of Patent: Jan. 1, 2019

(54) PROCESSES TO MAKE ALKYLATE GASOLINE BY SULFUR-CONTAMINATED IONIC LIQUID CATALYZED ALKYLATION

(71) Applicant: Chevron U.S.A. Inc., San Ramon, CA (US)

(72) Inventors: Hye-Kyung Cho Timken, Albany, CA (US); Bong-Kyu Chang, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/473,738

(22) Filed: Mar. 30, 2017

(65) Prior Publication Data

US 2017/0204340 A1    Jul. 20, 2017

Related U.S. Application Data

(62) Division of application No. 14/794,592, filed on Jul. 8, 2015.

(51) Int. Cl.
*C07C 2/58* (2006.01)
*C10G 50/00* (2006.01)
(Continued)

(52) U.S. Cl.
CPC .......... *C10G 50/00* (2013.01); *B01J 31/0284* (2013.01); *B01J 31/0298* (2013.01); *B01J 35/12* (2013.01);
(Continued)

(58) Field of Classification Search
None
See application file for complete search history.

(56) References Cited

U.S. PATENT DOCUMENTS 7,432,408 B2   10/2008   Timken et al.
8,183,425 B2   5/2012    Luo et al.
(Continued)

FOREIGN PATENT DOCUMENTS

CN   1257900 C   5/2006
CN   1786121 A   6/2006
(Continued)

OTHER PUBLICATIONS

Raymond F. Drnevich, et al.., "Cost Effective Technology for Organic Sulfur Removal from Refinery Fuel Gas", NPRA 2011 Meeting, San Antonio, Texas, Mar. 2011, pp. 1-7.
(Continued)

*Primary Examiner* — Philip Y Louie
(74) *Attorney, Agent, or Firm* — Susan Abernathy (57) ABSTRACT

Processes are provided for making an alkylate gasoline blending component, comprising:
  a. feeding an olefin feed comprising greater than 80 wppm of a sulfur contaminant comprising mercaptans, alkyl sulfides, and alkyl disulfides to a chloroaluminate ionic liquid catalyst, wherein a level of the sulfur contaminant accumulates in the chloroaluminate ionic liquid catalyst to make a sulfur-contaminated ionic liquid catalyst comprising 300 to 20,000 wppm of a sulfur; and
  b. alkylating the olefin feed with an isoparaffin using the sulfur-contaminated ionic liquid catalyst to make the alkylate gasoline blending component having a final boiling point below 221° C. An alkylation process exclusively utilizing coker LPG olefins is also provided.

19 Claims, 2 Drawing Sheets

(51) Int. Cl.
  *C10G 29/20* (2006.01)
  *C10G 11/18* (2006.01)
  *B01J 31/02* (2006.01)
  *B01J 35/12* (2006.01)
  *C10G 57/00* (2006.01)
  *C10L 1/02* (2006.01)
  *B01J 27/125* (2006.01)

(52) U.S. Cl.
  CPC ............... *C07C 2/58* (2013.01); *C10G 11/18* (2013.01); *C10G 29/205* (2013.01); *C10G 57/005* (2013.01); *C10L 1/023* (2013.01); *B01J 27/125* (2013.01); *C07C 2527/125* (2013.01); *C10G 2300/202* (2013.01); *C10G 2400/02* (2013.01); *C10L 2270/023* (2013.01); *C10L 2290/08* (2013.01)

(56) References Cited

U.S. PATENT DOCUMENTS

| | | |
|---|---|---|
| 8,247,628 B2 | 8/2012 | Hommeltoft et al. |
| 8,288,601 B2 | 10/2012 | Hommeltoft et al. |
| 8,728,301 B2 | 5/2014 | Timken |
| 8,795,515 B2 | 8/2014 | Zhan et al. |
| 8,865,960 B2 | 10/2014 | Timken et al. |
| 2004/0045874 A1 | 3/2004 | Olivier-Bourbigou et al. |
| 2009/0107032 A1* | 4/2009 | Lacheen ............ C10L 1/06 44/304 |
| 2009/0171134 A1 | 7/2009 | Luo et al. |
| 2009/0270667 A1 | 10/2009 | Elomari et al. |
| 2010/0147740 A1 | 6/2010 | Elomari et al. |
| 2010/0270211 A1 | 10/2010 | Wolny |
| 2011/0105811 A1 | 5/2011 | O'Rear et al. |
| 2011/0319693 A1 | 12/2011 | Hommeltoft et al. |
| 2012/0004096 A1 | 1/2012 | Hommeltoft |
| 2012/0024750 A1 | 2/2012 | Zhan et al. |
| 2012/0296145 A1 | 11/2012 | Lacheen |
| 2013/0062253 A1 | 3/2013 | Timken |
| 2013/0066130 A1 | 3/2013 | Luo et al. |
| 2013/0066133 A1 | 3/2013 | Cleverdon et al. |
| 2013/0209324 A1 | 8/2013 | Timken et al. |
| 2013/0211175 A1 | 8/2013 | Timken et al. |
| 2014/0350321 A1 | 11/2014 | Timken et al. |
| 2015/0025284 A1 | 1/2015 | Lowe et al. |
| 2015/0025285 A1 | 1/2015 | Cleverdon |

FOREIGN PATENT DOCUMENTS

| | | |
|---|---|---|
| CN | 101210199 B | 12/2010 |
| WO | 2009058517 A1 | 5/2009 |
| WO | 2011090611 A2 | 7/2011 |

OTHER PUBLICATIONS

Selexsorg aluminia-based adsorbent, 2014 https://www.basf.cagroup/corporate/ca/en/brand/SELEXSORB.

* cited by examiner

PROCESSES TO MAKE ALKYLATE GASOLINE BY SULFUR-CONTAMINATED IONIC LIQUID CATALYZED ALKYLATION

This application is a divisional of U.S. patent application Ser. No. 14/794,592, published as US20170007993A1, filed Jul. 8, 2015, in Group Art Unit 1732; and herein incorporated in its entirety.

TECHNICAL FIELD

This application is directed to a sulfur-contaminated ionic liquid catalyst useful for making alkylate gasoline blending components, a process for making alkylate gasoline blending components using a sulfur-contaminated ionic liquid catalyst, a method to construct a refinery alkylation unit with an ionic liquid alkylation reactor comprising an inlet that feeds a pure coker LPG olefin, and an alkylation process exclusively utilizing coker LPG olefins.

BACKGROUND

Improved alkylation catalysts, processes for using them, as well as methods to construct alkylation units in refineries are needed to utilize feeds comprising sulfur species that would: normally produce hydrocarbon products containing undesirable high sulfur, normally produce hydrocarbon products with high final boiling points, or quickly deactivate the alkylation catalyst.

SUMMARY

This application provides a sulfur-contaminated ionic liquid catalyst, comprising 300 to 20,000 weight parts per million (wppm) of a sulfur from a sulfur contaminant, wherein the sulfur-contaminated ionic liquid catalyst is a chloroaluminate and the sulfur-contaminated ionic liquid catalyst can alkylate an olefin and an isoparaffin to make an alkylate gasoline blending component having a final boiling point below 221° C. (430° F.).

This application provides a process for making an alkylate gasoline blending component, comprising:

a. feeding an olefin feed comprising greater than 80 wppm of a sulfur contaminant to an ionic liquid catalyst that is a chloroaluminate, wherein a level of the sulfur contaminant accumulates in the ionic liquid catalyst to make a sulfur-contaminated ionic liquid catalyst comprising 300 to 20,000 wppm of a sulfur from the sulfur contaminant; and b. alkylating the olefin feed with an isoparaffin using the sulfur-contaminated ionic liquid catalyst to make the alkylate gasoline blending component having a final boiling point below 221° C. (430° F.).

This application provides a method to construct a refinery alkylation unit, comprising: installing an ionic liquid alkylation reactor comprising an ionic liquid catalyst and wherein the ionic liquid alkylation reactor comprises an inlet that feeds a coker LPG olefin to the ionic liquid alkylation reactor without mixing the coker LPG olefin with other olefin feeds such that the coker LPG olefin makes a sulfur-contaminated ionic liquid catalyst; wherein the coker LPG olefin comprises from greater than 80 to 500 wppm of organic sulfur species and at least 20 wt % C3 and C4 olefins; and wherein an effluent from the ionic liquid alkylation reactor comprises an alkylate gasoline blending component having a final boiling point below 221° C. (430° F.).

This application also provides an alkylation process exclusively utilizing coker LPG olefins, comprising:

a. treating a coker LPG stream containing olefins with an amine treater, a caustic treater, or a combination thereof, to produce a treated coker LPG stream having a total sulfur content from 80 to less than 500 wppm and a total mercaptans content from 10 to 150 wppm;

b. drying the treated coker LPG stream to produce a dried coker LPG stream having from zero to less than 1 wppm water, from zero to 20 wppm total mercaptans, greater than 80 wppm total sulfur, and from zero to less than 100 wppm total oxygenates;

c. feeding the dried coker LPG stream, unmixed with any other olefins, and an isobutane to an alkylation reactor containing an ionic liquid catalyst, wherein the ionic liquid catalyst becomes a sulfur-contaminated ionic liquid catalyst; and d. alkylating the olefins with the isobutane using the sulfur-contaminated ionic liquid catalyst to make an alkylate gasoline blending component having a final boiling point below 221° C. (430° F.).

The present invention may suitably comprise, consist of, or consist essentially of, the elements in the claims, as described herein.

GLOSSARY

"Alkylating" refers to reaction of olefins and isoparaffins where the alkyl group and hydrogen from the isoparaffin molecules are added to the olefinic double bounds of the olefin molecules to produce higher molecular weight hydrocarbons.

"Sulfur-contaminated" refers to an increase in sulfur that occurs after the manufacture of a material and that is due to contact with a different material that introduces the sulfur as a sulfur contaminant.

"Ionic liquid catalyst" refers to a catalytic complex of at least two components that when mixed together are liquid below 100° C., have low vapor pressure, and include an organic cation and an anionic compound.

"Chloroaluminate" refers to an anionic compound comprising both chlorine and aluminum. Examples include $Al_2Cl_7^-$, $AlCl_4^-$, and $Al_3Cl_{10}^-$.

"Alkylate gasoline blending component" refers to a hydrocarbon produced by an alkylation reaction that can be blended into gasoline or used directly as gasoline. Examples of alkylate gasoline blending components are naphtha and heavy naphtha. In the context of this disclosure, naphtha has a boiling range distribution from 50 to 130° C. (~125-265° F.) and heavy naphtha has a boiling range distribution from 130 to 225° C. (265-430° F.).

"TBP" refers to the boiling point of a hydrocarbonaceous feed or product, as determined by ASTM D86-12

"Cut point" refers to the temperature on a True Boiling Point (TBP) curve at which a predetermined degree of separation is reached. Cut points disclosed herein include initial boiling point (IBP), T5, T10, T30, T50, T70, T90, T95 and FBP.

"Final boiling point (FBP)" refers to the highest temperature to boil off the hydrocarbon product via atmospheric distillation per procedure of ASTM D86-12.

An oil barrel (abbreviated as bbl) is a unit of volume defined as 42 US gallons, which is about 159 liters.

"Liquified petroleum gas" (LPG) refers to flammable mixtures of light hydrocarbons, including propane and butane. In the context of this disclosure, LPG also comprises $C_3$ and $C_4$ olefins.

"Wppm" refers to parts per million by weight.

DETAILED DESCRIPTION

The sulfur-contaminated ionic liquid catalyst comprises a level of sulfur from a sulfur contaminant that is greater than 200 wppm, such as from 300 to 20,000 wppm, or from 1000 to 10,000 wppm. The level of sulfur is measured by hydrolyzing the sulfur-contaminated ionic liquid catalyst and measuring the dissolved sulfur in water by inductively coupled plasma (ICP), such as by ASTM D1976-12. The sulfur-contaminated ionic liquid catalyst, unlike previously known acid catalysts used for isoparaffin alkylation, remains highly active for alkylating olefins and isoparaffins and makes an alkylate gasoline blending component having desired properties.

Sulfur Contaminant:

The sulfur contaminant can come from a broad range of refinery gas or liquefied petroleum gas (LPG) streams comprising olefins, such as from coker offgas, coker LPG, fluid catalytic cracker (FCC) LPG, FCC offgas, hydrocracker gas, and distillation gas. In one embodiment, the sulfur contaminant comprises sulfur species found in FCC olefin feed or coker olefin feed.

In one embodiment, an olefin feed comprising the sulfur contaminant is treated with an adsorbent prior to it being fed to the ionic liquid catalyst. The adsorbent can dry the hydrocarbon feed and also can reduce other impurities.

In one embodiment, the sulfur contaminant comprises sulfur species that form during treatment with a selective adsorbent that dries the olefin feed. Examples of selective adsorbents used to dry olefin feeds are alumina-silicates, active bentonite, metal oxide-based products, alumina powders, promoted alumina-based, activated carbon, and alumina Claus catalysts. In one embodiment the selective adsorbent is BASF Selexsorb® CD, which is a smooth, spherical promoted alumina-based adsorbent that is customized to provide optimum adsorption for several polar organic compounds including: oxygenated hydrocarbons, water, mercaptans, and nitrogen-based molecules. An example of a sulfur species that can be formed during treatment with a selective adsorbent that dries the olefin feed is methyl tert-butyl sulfide.

In one embodiment, the sulfur contaminant comprises one or more of methyl mercaptan, ethyl mercaptan, dimethyl sulfide, methyl tert-butyl sulfide, dimethyl disulfide, diethyl disulfide, and methyl ethyl disulfide. In one embodiment, the sulfur contaminant comprises mercaptans, alkyl sulfides, and alkyl disulfides.

Alkylation Unit Dedicated to Handle Exclusively Coker Olefin Feed

A coker or coker unit is an oil refinery processing unit that converts the residual oil from a vacuum distillation column or an atmospheric distillation column into low molecular weight hydrocarbon gases, naphtha, light and heavy gas oils, and petroleum coke. The coking process thermally cracks the long chain hydrocarbon molecules in the residual oil feed into shorter chain molecules leaving behind the excess carbon in the form of petroleum coke. The hydrocarbon product streams from the coker unit can be sent to various refinery units for further treating and then incorporated to gasoline, jet and diesel products.

Conventional refinery paraffin alkylation processes with $H_2SO_4$ or HF acid catalysts, typically use FCC LPG as the olefin feed source and a purified isobutane (>80% purity iC4) as the isoparaffin feed source. The olefin feeds are often treated to remove impurities to protect the alkylation catalysts and to reduce acid catalyst consumption. HF alkylation processes often include feed treating steps to remove moisture, sulfur and butadiene contents. The reduction of moisture and butadiene contents reduces the acid catalyst consumption for the $H_2SO_4$ alkylation process.

The coker unit produces substantial amounts of $C_3$-$C_4$ LPG range olefinic streams and $C_1$-$C_2$ hydrocarbon-containing offgas. Compared to the typical alkylation plant feed derived from a FCC LPG stream, the coker LPG contains significantly higher amounts of undesirable impurities such as butadiene (0.3-0.4 wt % vs. 0.1 wt %), oxygenates (500+ ppm vs. less than 100 ppm) and sulfur (280+ ppm vs. less than 100 Ppm).

Sulfuric acid alkylation processes would be able to handle high sulfur, above 100 ppm, but the high diene content of coker LPG olefin feed adversely impacts the alkylation performance, produces unacceptably high end-point, low octane, alkylate and increases the acid catalyst consumption to an unacceptable level. The hydrofluoric acid alkylation process needs to have very low sulfur feed, typically less than 10 ppm, otherwise the conjunct polymer formation increases and negatively affects the plant operability. Thus, in order to mitigate the impact of the high impurities, the conventional alkylation processes only handle very small amounts of coker LPG as a co-feed along with other feeds, such as a FCC olefin co-feed.

Some modern refineries do not have a FCC plant and have only a hydrocracking unit and coker unit, as the world-wide gasoline demand has declined while the jet and diesel demand have increased. For these refineries, an alkylation unit that utilizes the coker LPG feed exclusively, without mixing with any other olefin feeds, to make high quality alkylate gasoline or diesel would provide valuable new upgrading opportunities. We have discovered an ionic liquid catalyst is able to alkylate a coker olefins feedstock to make quality alkylate products without getting impacted by the feed impurities.

In one embodiment, the alkylation process exclusively utilizing coker LPG olefins or the process for making an alkylate gasoline blending component described herein comprises treating a coker LPG stream containing olefins to produce a treated coker LPG stream having from 80 to less than 500 wppm total sulfur. This treating can be done in an amine treater a caustic treater, or a combination thereof.

In one embodiment, the alkylation process exclusively utilizing coker LPG olefins or the process for making an alkylate gasoline blending component described herein comprises drying the treated coker LPG stream described above to produce a dried coker LPG stream having from zero to less than 1 wppm water, from zero to 20 wppm total mercaptans, greater than 80 wppm total sulfur, and from zero to less than 100 wppm total oxygenates.

In one embodiment, the alkylation process exclusively utilizing coker LPG olefins or the process for making an alkylate gasoline blending component described herein comprises feeding a dried coker LPG stream, unmixed with any other olefins, and an isoparaffin (such as isobutane) to an alkylation reactor containing an ionic liquid catalyst, wherein the ionic liquid catalyst becomes a sulfur-contaminated ionic liquid catalyst that remains effective for performing alkylation, and without causing excessive olefin oligomerization or unacceptably high acid catalyst consumption.

Olefin Feed:

The olefin feed comprising a sulfur contaminant is one that can be alkylated with an isoparaffin to make an alkylate gasoline blending component. The olefins in the olefin feed can comprise $C_2$-$C_6$ olefins and mixtures thereof, for example. In one embodiment the olefin feed comprises $C_3$ and $C_4$ olefins. In one embodiment the olefin feed comprises greater than 10 wt % $C_3$ and $C_4$ olefins, such as greater than 20 wt % up to 100 wt % $C_3$ and $C_4$ olefins. The olefin feed can also comprise hydrocarbon diluents, such as normal paraffins. The amount of the sulfur contaminant in the olefin feed can vary from greater than 80 wppm to 2000 wppm, such as from 100 to 1000 wppm, or from greater than 80 wppm to 500 wppm. In one embodiment, the olefin feed comprising the sulfur contaminant comes from a refinery and comprises 100 to 1000 wppm of organic sulfur species and at least 20 wt % $C_3$ and $C_4$ olefins.

In one embodiment, the olefin feed comprising a sulfur contaminant is a coker liquefied petroleum gas (LPG) olefin comprising the following hydrocarbons:

TABLE 1

Hydrocarbons in Coker LPG Olefin Feed

| Components | Wt % |
| --- | --- |
| Propane ($C_3$) | 10.0-25.0 |
| Propene ($C_3=$) | 4.0-8.0 |
| Isobutane (i$C_4$) | 6.0-12.0 |
| n-Butane (n$C_4$) | 25.0-40.0 |
| 1-Butene (1-$C_4=$) | 8.0-11.0 |
| 2-Methylpropene (i$C_4=$) | 5.0-10.0 |
| trans-2-Butene (t-2-$C_4=$) | 3.0-7.0 |
| Cis-2-Butene (c-2-$C_4$) | 2.0-5.0 |
| 1-3-Butadiene (1-3-$C^4$DE) | 0.0-1.0 |
| Isopentane (i$C_5$) | 0.5-5.0 |
| n-Pentane (n$C_5$) | 0.0-1.0 |
| $C_5^+$ | 1.1-3.0 |
| Total | 100.0 |
| Total $C_3=$ | 4.0-12.0 |
| Total $C_4=$ | 18.0-30.0 |
| Total Olefins | 22.0-42.0 |

The gas chromatography test method used to identify and quantify the hydrocarbons in the coker LPG olefin was ASTM D2163-14.

In one embodiment, the olefin feed comprises from 0 to 5 wppm water.

Isoparaffin Feed:

The isoparaffin feed that can be alkylated includes $C_3$-$C_7$ isoparaffins, and mixtures thereof. In one embodiment, the isoparaffin feed comprises a sulfur contaminant. In one embodiment, the isoparaffin feed comprises isobutane. In one embodiment, the isoparaffin feed is produced in a refinery. In one embodiment, the isoparaffin feed comprises from 50 to 95 wt % isobutane, and from 5 to 50 wt % n-butane. In one embodiment, the isoparaffin feed is dried to have from zero-5 wppm water before it is fed to the ionic liquid catalyst or to the alkylation reactor containing the ionic liquid catalyst.

Alkylating:

The alkylating can be performed in an ionic liquid alkylation reactor under conditions known to produce alkylate gasoline. The alkylation conditions in the alkylation reactor can be selected to provide the desired product yields and quality.

In one embodiment the alkylating is carried out in a liquid hydrocarbon phase, in a batch system, a semi-batch system, or a continuous system. Ionic liquid catalyst volume in the alkylation reactor can be in the range of 0.5 vol % to 80 vol %, for example from 1 vol % to 25 vol %, or from 2 vol % to 10 vol %. In some embodiments, vigorous mixing can be used to provide good contact between the olefins, the isoparaffins, and the ionic liquid catalyst. In one embodiment the temperature during the alkylating can be in the range from −40° C. to 150° C., such as −20° C. to 100° C., or −15° C. to 50° C. The pressure during the alkylating can be in the range from atmospheric pressure to 8000 kPa. In one embodiment the pressure is kept at a high enough level to keep the reactants in the liquid phase. The residence time of reactants in the alkylation reactor can be in the range of a second to 60 hours.

In one embodiment, the molar ratio of isoparaffin to olefin during the alkylating can vary over a broad range. In one embodiment the molar ratio of isoparaffin to olefin is in the range of from 0.5:1 to 100:1. For example, in different embodiments the molar ratio of isoparaffin to olefin is from 1:1 to 50:1, 5:1 to 20:1, 8:1 to 12:1, or 4:1 to 10:1.

Ionic Liquid Catalyst:

The ionic liquid catalyst used in the processes and compositions described herein is composed of at least two components which form a complex. In one embodiment, the ionic liquid catalyst comprises a first component and a second component.

In one embodiment, the first component of the ionic liquid catalyst comprises a Lewis Acid. In one embodiment, the Lewis Acid is a metal halide compound selected from components such as Lewis Acidic compounds of Group 13 metals, including aluminum halides, alkyl aluminum halide, gallium halide, and alkyl gallium halide. In one embodiment, the Lewis Acidic compound is a Group 3, 4, or 5 metal halide. Examples of these types of metal halides include $ZrCl_4$, $HfCl_4$, $NbCl_5$, $TaCl_5$, $ScCl_3$, $YCl_3$, and mixtures thereof. The periodic table by the International Union of Pure and Applied Chemistry (IUPAC), version date 22 Jun. 2007, is used for defining the Groups 3, 4, 5, and 13 metals. In one embodiment, the first component is aluminum halide or alkyl aluminum halide. In one embodiment, aluminum trichloride is the first component of the ionic liquid catalyst.

In one embodiment, the second component of the ionic liquid catalyst is an organic salt or a mixture of salts. These salts can be characterized by the general formula Q+A−, wherein Q+ is an ammonium, phosphonium, or sulphonium cation and A− is a negatively charged ion such as Cl−, Br−, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, alkyl-aryl sulfonate, and benzene sulfonate (e.g., 3-sulfurtrioxyphenyl), where R is an alkyl group with 1-12 carbon atoms. In one embodiment, the second component is selected from those having quaternary ammonium halides containing one or more alkyl moieties having from 1 to 12 carbon atoms, such as, for example, trimethylamine hydrochloride, methyltributylammonium halide, or substituted heterocyclic ammonium halide compounds, such as hydrocarbyl substituted pyridinium halide compounds, for example 1-butylpyridinium halide, benzylpyridinium halide, or hydrocarbyl substituted imidazolium halides, such as for example, 1-ethyl-3-methylimidazolium chloride.

In one embodiment, the ionic liquid catalyst is a conjunct polymer based ionic liquid, such as described in US20130190167A1.

In one embodiment, the ionic liquid catalyst is a chloroaluminate. For example, the ionic liquid catalyst can be selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. In one embodiment, the ionic liquid catalyst is an acidic haloaluminate ionic liquid, such as an alkyl substituted pyridinium chloroaluminate or an alkyl substituted imidazolium chloroaluminate of the general formulas A and B, respectively.

In the formulas A and B; R, $R_1$, $R_2$, and $R_3$ are each independently H, methyl, ethyl, propyl, butyl, pentyl or hexyl group, and X is a chloroaluminate. In the formulas A and B, R, $R_1$, $R_2$, and $R_3$ may or may not be the same. In one embodiment the ionic liquid catalyst is N-butylpyridinium chloroaluminate.

In one embodiment the ionic liquid catalyst comprises a cation selected from the group of an alkyl-pyridinium, an alkyl-imidazolium, or a mixture thereof. In another embodiment the ionic liquid catalyst can have the general formula $RR'R''NH^+Al_2Cl_7^-$, wherein N is a nitrogen containing group, and wherein R, R' and R'' are alkyl groups containing 1 to 12 carbons, and where R, R' and R'' may or may not be the same.

The presence of the first component can give the ionic liquid catalyst a Lewis acidic character. In one embodiment the ionic liquid catalyst includes strongly Lewis acidic anions, such as $Al_2Cl_7^-$. $Al_2Cl_7^-$, for example, is a strongly Lewis acidic anion, while $AlCl_4^-$ is not.

In one embodiment, the greater the mole ratio of the first component to the second component, the greater is the acidity of the acidic ionic liquid catalyst.

Other examples of compounds which can be used as the ionic liquid catalyst include: 1-Butyl-3-methylimidazolium hexafluorophosphate [$bmim^+$][$PF_6^-$], Trihexyl(tetradecyl)phosphonium chloride [$thtdP^+$][$Cl^-$], commercially available as CYPHOS IL 101™ (Hydrocarbon soluble (hexane, toluene) Tg-56° C.), and 1-Ethyl-3-methylimidazolium tetrachloroaluminate [$emim^+$][$AlCl_4^-$]. In one embodiment, the second component in the ionic liquid catalyst can be Trihexyl(tetradecyl)phosphonium chloride [$thtdP^+$][$Cl^-$].

In one embodiment, the ionic liquid catalyst comprises metal halides, such as $AlCl_3$, $AlBr_3$, $Al_2Cl_7$, $GaCl_3$, $GaBr_3$, $InCl_3$, and $InBr_3$.

Co-Catalyst:

In one embodiment, the sulfur-contaminated ionic liquid catalyst will additionally comprise a co-catalyst that promotes the alkylating of the olefin feed and the isoparaffin. The co-catalyst can comprise, for example, HCl, or organic chloride, or hydrogen halides, or organic halides, wherein halides include Cl, Br, or I ions. In one embodiment, the co-catalyst is anhydrous HCl. When organic chloride is used as the co-catalyst with the ionic liquid catalyst, HCl may be formed in situ in a reactor during the alkylating. It is believed that the organic halide decomposes under hydrocarbon conversion conditions to liberate Bronsted acids or hydrogen halides, such as hydrochloric acid (HCl) or hydrobromic acid (HBr). These Bronsted acids or hydrogen halides promote the alkylation reaction.

In one embodiment the halide in the hydrogen halide or an alkyl halide is the same as a halide component of the ionic liquid catalyst. In one embodiment the alkyl halide is an alkyl chloride, for example t-butyl chloride or n-butyl chloride. A hydrogen chloride or an alkyl chloride can be used advantageously with an ionic liquid catalyst that is a chloroaluminate.

In one embodiment, the co-catalyst comprises an alkyl halide that is derived from the isoparaffin and olefins used in the alkylation reaction. For example, for the alkylation of isobutane with butenes using a chloroaluminate ionic liquid catalyst, the co-catalyst could be 1-butyl chloride, 2-butyl chloride or tertiary butyl chloride, or a combination of these chlorides. In one embodiment, the alkyl chloride co-catalyst is a derivative of the olefin stream to, in theory, invoke hydride transfer and the participation of the isoparaffin. When used, the alkyl halide co-catalyst is used in catalytic amounts. In one embodiment, the alkyl halide co-catalyst should be kept at low concentrations and not exceed the molar concentration of content of $AlCl_3$ in the ionic liquid catalyst. The amounts of the alkyl halides used may range from 0.001 mol %-100 mol % of the Lewis acid $AlCl_3$ in the ionic liquid catalyst. Concentrations of the alkyl halides in the range of 0.001 mol %-10 mol % of the $AlCl_3$ can provide the acidity of the ionic liquid catalyst at the desired performing capacity. In one embodiment, the amount of the alkyl halide co-catalyst can be proportional to the amount of olefin in the olefin feed and not exceed the molar concentration of the olefin in the olefin feed.

In some embodiments, the co-catalyst is a Bronsted acid. A Bronsted acid is any substance that can donate an $H^+$ ion to a base. Bronsted acids are $H^+$-ion or proton donors. Examples of Bronsted acids are HCl, HBr, HI, HF, sulfuric acid, and mixtures thereof. In one embodiment, the co-catalyst enhances the activity of the sulfur-contaminated ionic liquid catalyst and improves the yield of the alkylate gasoline blending component.

In one embodiment, the molar ratio of the olefin feed to the co-catalyst during the alkylating is from 10 to 200.

Alkylate Gasoline Blending Component:

The alkylate gasoline blending component has a final boiling point below 221° C. (430° F.), which demonstrates that the alkylation is well controlled. In one embodiment, the alkylate gasoline blending component has a final boiling point from 191 to 207° C. (376 to 404° F.). In one embodiment, the alkylate gasoline blending component has a Research Octane Number (RON) from 80 to 105. RON can be measured by ASTM D2699-13b.

Process for Making Alkylate Gasoline Blending Component:

The process for making an alkylate gasoline blending component, comprises:

a. feeding an olefin feed comprising greater than 80 wppm of a sulfur contaminant to an ionic liquid catalyst that is a chloroaluminate, wherein a level of the sulfur contaminant accumulates in the ionic liquid catalyst to make a sulfur-contaminated ionic liquid catalyst comprising 300 to 20,000 wppm of a sulfur from the sulfur contaminant; and b. alkylating the olefin feed with an isoparaffin using the sulfur-contaminated ionic liquid catalyst to make the alkylate gasoline blending component having a final boiling point below 221° C. (430° F.).

In one embodiment, the olefin feed can be fed directly from a refinery process unit that produces the olefin feed without any additional steps to further reduce the amount of the sulfur contaminant in the olefin feed. In one embodiment, the only clean-up step is drying of the olefin feed to remove water before it is fed to the ionic liquid catalyst. In one embodiment, the olefin feed comprising the sulfur contaminant is dried using a selective adsorbent. In one embodiment, the selective adsorbent dries and maintains the level of water in the olefin feed from 0 to 5 wppm, or less than 1 wppm.

The alkylating can be performed continuously because the sulfur-contaminated ionic liquid catalyst remains effective to perform the alkylating over the full range of 300 to 20,000 wppm of the sulfur contaminant in the ionic liquid catalyst. In one embodiment, the alkylating is performed continuously for one to 600 days, such as from one to 365 days.

In one embodiment, the process additionally comprises continuously sending a portion of the sulfur-contaminated ionic liquid catalyst to a regeneration reactor to regenerate the sulfur-contaminated ionic liquid catalyst and to maintain 0.5 to 10 wt % of a conjunct polymer in the sulfur-contaminated ionic liquid catalyst during the alkylating. In one embodiment, the regeneration reactor is a hydro-regeneration reactor. Examples of reactors and processes for regenerating used ionic liquid catalysts are described in US20070142213A1 and U.S. Pat. No. 8,884,091B2. The level of conjunct polymer can be determined by hydrolysis of known weights of the sulfur-contaminated ionic liquid catalyst as described in US20070142213A1, or by vibrational spectroscopy as described in US20120296145A1.

Method to Construct a Refinery Alkylation Unit:

This application provides a method to construct a refinery alkylation unit, comprising: installing an ionic liquid alkylation reactor comprising an ionic liquid catalyst and wherein the ionic liquid alkylation reactor comprises an inlet that feeds a coker LPG olefin to the ionic liquid alkylation reactor without mixing the coker LPG olefin with other olefin feeds such that the coker LPG olefin makes a sulfur-contaminated ionic liquid catalyst; wherein the coker LPG olefin comprises from greater than 80 to 500 wppm of organic sulfur species and at least 20 wt % C3 and C4 olefins; and wherein an effluent from the ionic liquid alkylation reactor comprises an alkylate gasoline blending component having a final boiling point below 221° C. (430° F.).

In one embodiment, an existing HF or $H_2SO_4$ refinery alkylation unit can be retrofitted to better utilize coker LPG olefins by replacing an existing HF or $H_2SO_4$ alkylation reaction and installing in its place an ionic liquid alkylation reactor comprising an ionic liquid catalyst.

The ionic liquid alkylation reactor comprises an inlet that feeds a coker LPG olefin to the ionic liquid alkylation reactor without mixing the coker LPG olefin with any other olefin feeds. In one embodiment, the coker LPG olefin comprises from greater than 80 to 500 wppm of organic sulfur species and at least 20 wt % $C_3$ and $C_4$ olefins.

In one embodiment, the ionic liquid alkylation reactor that can be used is one capable of forming a homogeneous reaction mixture comprising a dispersed ionic liquid catalyst phase and a continuous hydrocarbon phase. As an example, a homogeneous reaction mixture can comprise an emulsion comprising small droplets of ionic liquid catalyst suspended in the hydrocarbon phase to provide a homogeneous emulsion. In one embodiment the ionic liquid alkylation reactor is a supported ionic liquid alkylation reactor, such as described in U.S. Pat. No. 8,388,903. Other suitable ionic liquid alkylation reactors include continuous stirred tank reactors, in-line mixers, and nozzle reactors.

In one embodiment, the method to construct a refinery alkylation unit additionally comprises installing a drier unit comprising a selective adsorbent that dries the coker LPG olefin between the effluent port of a coker unit and the inlet that feeds the coker LPG olefin to the ionic liquid alkylation reactor. Examples of suitable selective adsorbents were disclosed earlier in this disclosure. In another embodiment, the method comprises installing an isomerization reactor between the drier unit and the inlet that feeds the coker LPG olefin to the ionic liquid alkylation reactor.

EXAMPLES

N-butylpyridinium chloroaluminate ($C_5H_5NC_4H_9Al_2Cl_7$) was the ionic liquid catalyst used in the examples below. This ionic liquid catalyst had the following initial elemental composition and had a density of 1.34 g/cc.

TABLE 2

| Ionic Liquid Catalyst Composition | |
|---|---|
| Element | Wt % |
| Al | 12.4 |
| Cl | 56.5 |
| C | 24.6 |
| H | 3.2 |
| N | 3.3 |

Example 1: Coker LPG and Fluid Catalytic Cracker (FCC) LPG Olefin Feeds

Three cylinders of coker LPG containing a mixture of $C_3$ and $C_4$ olefins were obtained from a coker unit in a refinery from a sample point located at the downstream of the Coker LPG Caustic Treater and a MEROX® Treater. MEROX is a registered trademark of UOP's desulfurization processes, catalysts, and technical services. A cylinder of FCC $C_3/C_4$ LPG was obtained from a FCC unit in a refinery from a sample point located downstream of both a FCC LPG Caustic Treater followed by a MEROX Treater.

The properties of the different LPG samples were evaluated by gas chromatography for composition, sulfur and oxygenate contents, and the results are summarized in Table 3. The test method used to quantify the oxygenate content in LPG olefin feeds was ASTM D7423-09 (Reapproved 2014).

The sulfur quantitation and species were measured with gas chromatograph using an ASTM test method for sulfur species, ASTM D5623-94 (Reapproved 2014). The GC column was completely flushed after each sample was injected until it was confirmed that no peaks from the previous sample appeared from the column before another sample was injected.

Compared with the FCC LPG, the as-received coker LPG samples contained substantially lesser amount of total olefins (~33 wt % vs.~42 wt %). The coker LPG samples also contained significantly higher amount of undesirable impurities such as butadiene (0.3-0.4 wt % vs. 0.1 wt %), oxygenate (500+ ppm vs. less than 100 ppm) and total sulfur (280+ ppm vs. less than 100 ppm). Due to the very high contents of impurities and lower olefin contents, the coker LPG streams as-is could not be processed in an alkylation unit without some additional treatment.

Example 2: Properties of Coker LPG Olefin Feed after Drying

The coker LPG stream samples from Example 1 were dried with an adsorbent and used as the olefin feed source in alkylation experiments. The concentrations of water, total sulfur, total oxygenates, and dienes in the coker LPG olefin feeds before and after drying are summarized in Table 3.

TABLE 3

Olefin Feed Compositions (Coker LPG Stream vs. FCC LPG Stream)

| | Coker LPG Olefins Cylinder 1 | Coker LPG Olefins Cylinder 2 | Coker LPG Olefins Cylinder 3 | FCC LPG Olefins |
|---|---|---|---|---|
| Sample Composition, wt % | | | | |
| Propane ($C_3$) | 22.8 | 17.4 | 21.6 | 8.3 |
| Propene ($C_3=$) | 6.7 | 5.3 | 6.6 | 20.2 |
| Isobutane ($iC_4$) | 7.2 | 7.8 | 8.5 | 34.2 |
| n-Butane ($nC_4$) | 32.5 | 36.0 | 31.7 | 10.2 |
| 1-Butene ($1\text{-}C_4=$) | 9.9 | 10.2 | 9.8 | 5.8 |
| 2-Methylpropene ($iC_4=$) | 7.3 | 7.4 | 7.2 | 5.6 |
| trans-2-Butene ($t\text{-}2\text{-}C_4=$) | 5.2 | 5.8 | 5.4 | 6.3 |
| Cis-2-Butene ($c\text{-}2\text{-}C_4$) | 3.7 | 4.2 | 3.9 | 4.3 |
| 1-3-Butadiene | 0.4 | 0.3 | 0.4 | 0.1 |
| Isopentane ($iC_5$) | 2.3 | 3.1 | 2.5 | 3.8 |
| n-Pentane ($nC_5$) | 0.4 | 0.4 | 0.4 | 0.1 |
| $C_5^+$ | 1.6 | 2.0 | 1.9 | 1.0 |
| Total | 100.0 | 100.0 | 100.0 | 100.0 |
| Total $C_3=$, wt % | 6.7 | 5.3 | 6.6 | 20.2 |
| Total $C_4=$, wt % | 26.1 | 27.7 | 26.3 | 22.0 |
| Total Olefins, wt % | 32.8 | 33.0 | 33.0 | 42.2 |
| Impurities in As-Received Feeds | | | | |
| Total Oxygenate, ppm | 569 | 549 | 567 | 70 |
| Total Sulfur, ppm | 289 | Not measured | 293 | ~60 |
| Impurities in Feeds After Drying | | | | |
| Water, ppm | 0.5 | 0.5 | 0.5 | <1 |
| Total Oxygenate, ppm | 40 | 38 | 319 | <10 |
| Total Sulfur, ppm | 115 | 139 | 293 | <10 |
| Butadiene, wt % | 0.4 | 0.3 | 0.4 | 0.1 |

The coker LPG olefin feeds were thoroughly dried and maintained at below 1 ppm water by passing the feeds through a fixed bed containing BASF SelexSorb® CD adsorbent at around 1-2 LHSV. In addition to removing water, the BASF SelexSorb® CD adsorbent removed oxygenates very effectively when the material was fresh, in that the oxygenate content was reduced from ~570 ppm to 40 and 38 ppm (Cylinders 1 and 2). For the dried sample from Cylinder 3, the adsorbent had been used up, such that the oxygenate content in the dried sample was 319 ppm and the sulfur content was about the same as in the original feed.

The water in the dried coker LPG olefin feeds was measured using on-line moisture probes with aluminum oxide type moisture sensors. The moisture probe openings were small in relation to the size of the organic molecules being tested and therefore, admissions into the sensor cavity were limited to much smaller molecules, such as water. The surface of the aluminum oxide sensor acted as a semi-permeable membrane, which permitted the measurement of water vapor pressure in the dried coker LPG olefin feeds (hydrocarbon liquid). The aluminum oxide sensor was directly immersed in the hydrocarbon liquid to measure the equivalent dew point. Since the dew point is functionally related to the vapor pressure of the water, the determination of the dew point allowed for the calculation of the wppm of water in the liquid by a Henry's Law type analysis (wppm=K*Pw, where K is the Henry's Law constant in the appropriate units and Pw is the water vapor pressure).

The sulfur species in one of the coker LPG olefin feeds before and after drying are reported in Table 4.

TABLE 4

Effect of Drying Coker LPG Feeds with Dryerant, Sulfur Speciation and Concentration of Sulfur

| Sulfur Speciation, wppm | As-Received | After Drying |
|---|---|---|
| Methyl Mercaptan | 29 | 2.7 |
| Ethyl Mercaptan | 46 | 1.6 |
| Dimethyl Sulfide | 30 | 3.3 |
| Carbon Disulfide | 0 | 0 |
| Ethyl Methyl Sulfide | 0 | 0 |
| Methyl Tert-Butyl Sulfide | 0 | 29 |
| Dimethyl Disulfide | 88 | 19 |
| Diethyl Disulfide | 16 | 0 |
| Methyl Ethyl Disulfide | 80 | 30 |
| Total Unknown Sulfur | 0 | 28 |

The results in Table 4 show that the drying step changed the nature of the sulfur species slightly. The dried coker LPG olefin feed still contained various organic sulfur species such as mercaptans, alkyl sulfides, and alkyl disulfides.

Example 3: Alkylation of Dried Coker LPG Olefin Feed after Isomerization (Invention)

Figure 1:
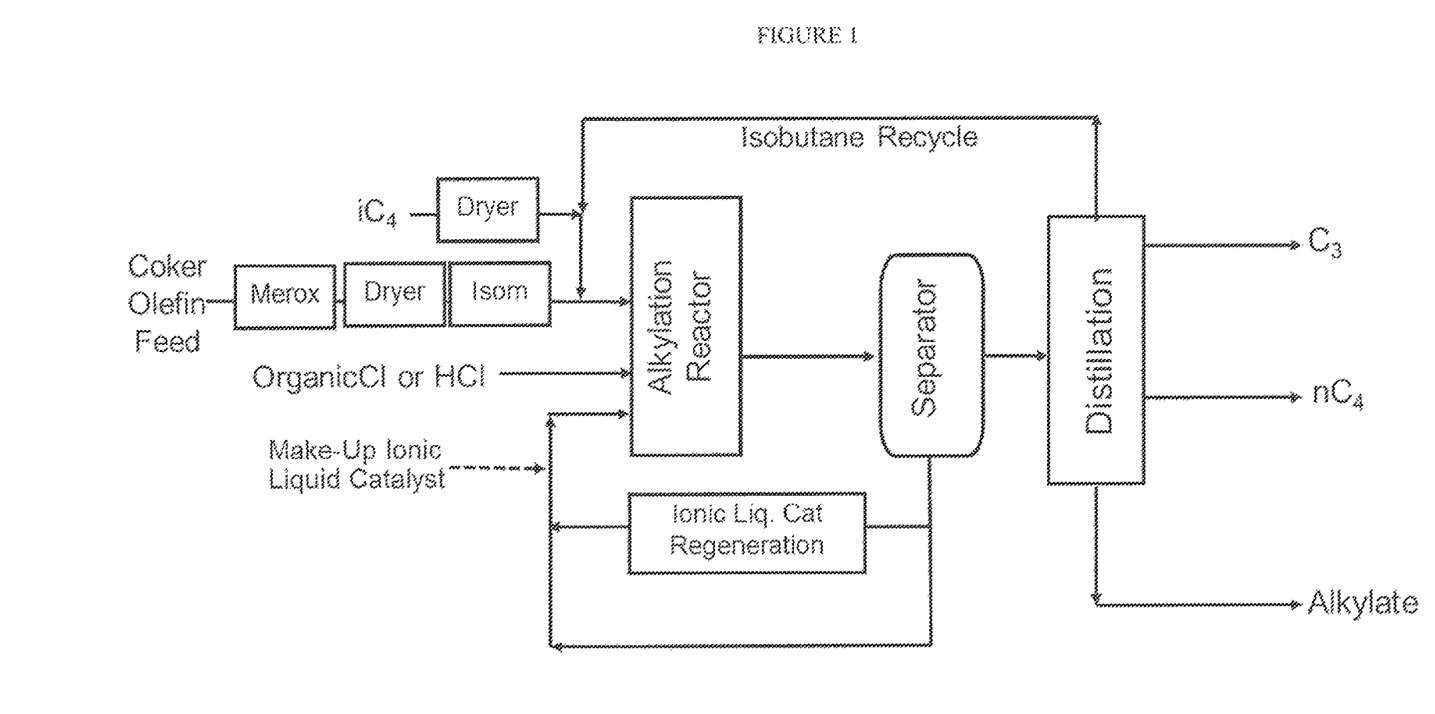
FIG. 1 is a process flow diagram of the research test unit used for the alkylation examples described herein.

Refinery isobutane containing 85% isobutane and 15% n-butane was used for this study. The refinery isobutane was dried with 13× molecular sieve. The dried coker LPG olefin stream containing $C_3$ and $C_4$ olefins from Example 2 was used as the olefin feed for alkylation, after an isomerization step. A simplified process flow diagram of this research test unit is shown in FIG. 1.

The coker LPG olefin feed from Example 2 was isomerized with a Pd/Al2O3 catalyst at 150° F., and 190 psig in the presence of hydrogen to produce isomerized $C_4$ and $C_3$ coker LPG olefin feed with the composition shown in Table 5.

TABLE 5

Composition of Coker LPG Olefin Feed

| Composition, wt % | As-Received | After Isomerization |
|---|---|---|
| Propane, $C_3$ | 22.8 | 24.0 |
| Propylene, $C_3=$ | 6.7 | 6.9 |
| 1-Butene, $1\text{-}C_4=$ | 9.9 | 1.5 |
| 2-Butene, $2\text{-}C_4=$ | 8.9 | 18.8 |
| 2-Methylpropene, $i\text{-}C_4=$ | 7.3 | 6.3 |
| 1,3-Butadiene, $C_4=$ | 0.4 | 0 |
| n-Butane, $nC_4$ | 32.5 | 27.4 |
| Isobutane, $iC_4$ | 7.2 | 10.0 |
| $C_5^+$ | 4.3 | 5.0 |
| Sum | 100.0 | 100.0 |
| Conversion of 1,3-Butadiene, % | Base | 100.0 |
| Isomerization of 1-Butene, % | Base | 84.6 |

Evaluation of $C_3/C_4$ coker LPG olefin alkylation with isobutane was performed in a 300 cc continuously stirred tank reactor stirring at 1600 RPM. A mixture of isobutane and olefin in 9.5:1 (I/O) molar ratio was fed to the alkylation reactor while vigorously stirring. An ionic liquid catalyst as described in Table 2 was fed to the reactor via a second inlet port targeted to occupy 6 vol % in the reactor. A small amount of n-butyl chloride was added to produce anhydrous HCl gas in situ. The average residence time in the alkylation reactor (combined volume of feeds and catalyst) was about 12 minutes. The outlet pressure was maintained at 150 psig and the alkylation reactor temperature was maintained at 95° F. (35° C.) using internal cooling coil.

The alkylation reactor effluent was separated with a coalescing separator into a hydrocarbon phase and an ionic liquid catalyst phase. The hydrocarbon phase was further separated with three distillation columns into multiple streams, including: a gas stream containing a $C_3^-$ fraction, an $nC_4$ stream, an $iC_4$ stream, and an alkylate stream. The ionic liquid catalyst was recycled back to the alkylation reactor for repeated use. To maintain the activity of the ionic liquid catalyst, the used ionic liquid catalyst was sent to a hydrogenation reactor for reduction of the conjunct polymer level in the ionic liquid catalyst. We maintained the conjunct polymer level of the ionic liquid catalyst at around 4% level with the hydrogenation. The amount of conjunct polymer in the ionic liquid catalyst was determined using an FT-IR quantitation method described in U.S. patent application Ser. No. 13/108,607, filed on May 16, 2011.

The detailed composition of the alkylate gasoline produced in this example was analyzed using gas chromatography. Research Octane and Motor Octane numbers were measured by an engine test. The operating conditions and product properties are summarized in Table 6. The term 'pure' refers to the conditions in Examples 3 and 4 where the coker LPG olefin feeds are not mixed or diluted with any other sources of olefins.

The results of Example 3, shown in Table 6, indicate that high octane alkylate can be obtained with coker LPG olefin feed via isomerization of the olefin feed using an isomerization catalyst followed by alkylation of isobutane using n-butylpyridinium chloroaluminate ionic liquid catalyst. With the $C_3/C_4$ coker LPG olefin feed, alkylate gasoline with 92.6 RON, 91.1 MON and 198° C. end point was obtained by isomerization of the feed.

TABLE 6

Continuous Alkylation of Coker LPG Olefin with Ionic Liquid Catalyst and Comparison with $H_2SO_4$ Process

|  | Example 3 Pure Dried Coker LPG after Isomerization | Example 4 Pure Dried Coker LPG without Isomerization | Example 5 50:50 Mix of FCC/Coker LPG |
|---|---|---|---|
| Feed Olefin Source |  |  |  |
| Feed Paraffin Source | 85% purity isobutane | 85% purity isobutane | 85% purity isobutane |
| Catalyst | $BupyAl_2C_7$ Ionic Liquid Cat | $BupyAl_2C_7$ Ionic Liquid Cat | $H_2SO_4$ Catalyst |
| Catalyst volume fraction in reactor | 0.06 | 0.06 | 0.50 |
| Temperature, ° C. | 35 | 35 | 15 |
| External I/O ratio, molar | 8 | 8 | 8 |
| Sulfur in Feed Olefin, ppm | 115 | 293 | ~200 |
| Oxygenate in Feed Olefin, ppm | 38 | 319 | ~200 |
| 1,3-Butadiene in Feed Olefin, wt % | 0 | 0.4 | ~0.2 |
| Olefin conversion, wt % | 99.5+ | 99.5+ | 99+ |
| $C_5^+$ Gasoline Composition |  |  |  |
| $C_5$ | 3.6 | 3.3 |  |
| $C_6$ | 5.5 | 4.0 |  |
| $C_7$ | 19.8 | 19.8 |  |
| $C_8$ | 53.1 | 50.4 |  |
| $C_9^+$ | 18.0 | 22.5 |  |
| Sum | 100.0 | 100.0 |  |
| C8 Product Isomer Distribution, wt % |  |  |  |
| % tri-Me-pentane/total C8 | 72.4 | 51.1 |  |
| % Di-Me-hexane/total C8 | 25.0 | 44.2 |  |
| % Me-Heptane/total C8 | 2.4 | 4.4 |  |
| % n-Octane/total C8 | 0.0 | 0.0 |  |
| Research Octane | 92.6 | 85.2 | 91 |
| Motor Octane | 91.1 | 86.0 |  |
| Distillation Temperature, ° C. |  |  |  |
| IBP | 37 | 35 | 51 |
| T10, wt % | 63 | 66 | 76 |
| T30, wt % | 96 | 98 | 87 |
| T50, wt % | 104 | 106 | 96 |
| T70, wt % | 112 | 115 | 111 |
| T90, wt % | 183 | 182 | 153 |
| FBP | 198 | 199 | 251 |

Example 4: Alkylation of Dried Coker LPG Olefin Feed without Isomerization (Invention)

Another alkylation experiment was conducted with the coker LPG olefin Cylinder #3 feed (from Table 3) with the conditions nearly identical to Example 3, except excluding a feed isomerization step.

Again, the detailed composition of the alkylate gasoline that was produced was analyzed using gas chromatography. Research Octane and Motor Octane numbers were measured by an engine test. The operating conditions and product properties are summarized in Table 6. With the C₃/C₄ coker LPG olefin feed without isomerization, the alkylate gasoline that was produced exhibited 85.2 RON, 86.0 MON and 199° C. (390° F.) end point.

Our alkylation study in this example showed that the coker LPG olefin feed from Cylinder 3, dried to <1 ppm water, 319 ppm total oxygenates, 0.4 wt % diene and 293 ppm total sulfur was alkylated well with a sulfur-contaminated ionic liquid catalyst to make a high quality alkylate with a low final boiling point. This result was completely unanticipated.

The results of Example 4, shown in Table 6, indicate that the Octane Number of the alkylate product is substantially lower than Example 3, suggesting that incorporation of an isomerization step is helpful if one desires to make high Octane Number alkylate. While there are substantial differences in Octane Numbers between Example 3 and 4, surprisingly, both examples show very similar boiling point distributions. Considering such a high content of diene for Example 4, and additional sulfur in the feed, obtaining the high yields of alkylate with nearly identical boiling point distributions was quite unexpected. The final boiling points of the alkylate gasoline blending components produced from the coker LPG olefins were comparable to those produced from FCC olefins in earlier studies using the same research test unit.

Example 5: Comparison with $H_2SO_4$ Alkylation of Coker LPG Olefin Feed (Comparative Example)

This example relates to a commercial $H_2SO_4$ alkylation unit where the olefin feed source is a 50:50 volume mix of FCC LPG and coker LPG. Due to the addition of coker LPG in the feed, the acid catalyst consumption more than doubled compared to a typical alkylation unit using FCC LPG olefin feed only. The operating conditions and product properties are summarized in Table 6.

The alkylate properties from the commercial $H_2SO_4$ alkylation unit using the mixed FCC LPG and coker LPG olefin feed, shown in Table 6, were far poorer than the process of our invention shown in Examples 3 and 4. The $H_2SO_4$ alkylation unit produced alkylate with final boiling points of 484 to 509° F. (251 to 265° C.) when using a 50:50 mix of FCC LPG and coker LPG as the olefin feed source, while the process of our invention showed about a 404° F. (207° C.) end point with a purer coker LPG olefin feed.

In addition, the acid consumption of the $H_2SO_4$ plant was very high (1 lb $H_2SO_4$/gal alkylate, about twice that of the FCC olefin only feed). The above results (high final boiling point of the alkylate and high acid catalyst consumption) clearly suggest that there is an opportunity for process improvement for alkylation of coker LPG olefin feed.

The results from Examples 3 and 4 vs. Example 5 clearly indicate our process with an ionic liquid catalyst produces far better quality alkylate with a tougher feed (50% coker LPG vs. 100% coker LPG) and provides a substantial process improvement over the conventional alkylation for processing coker LPG. Our process can be used to alkylate 100% pure coker LPG olefin steams as the olefin feed to an alkylation plant.

Example 6: Hydro-Regeneration of Ionic Liquid Catalyst and Extended Operation with Coker LPG Olefin Feed The alkylation process described in Examples 3 and 4 was maintained over 17 days while a portion of the ionic liquid catalyst separated by the coalescer described in Example 3 (and shown in FIG. 1) was continuously sent to a regeneration reactor to regenerate the ionic liquid catalyst and to maintain the level of conjunct polymer in the ionic liquid catalyst during the alkylation at less than 4 wt %. Over the 17 day course of the alkylation study, all of the alkylate gasoline samples collected had final boiling points from 191 to 207° C. (376 to 404° F.). The alkylate sample collected during the course of this study had Research Octane Numbers ranging from 85 to 93.

Figure 2:
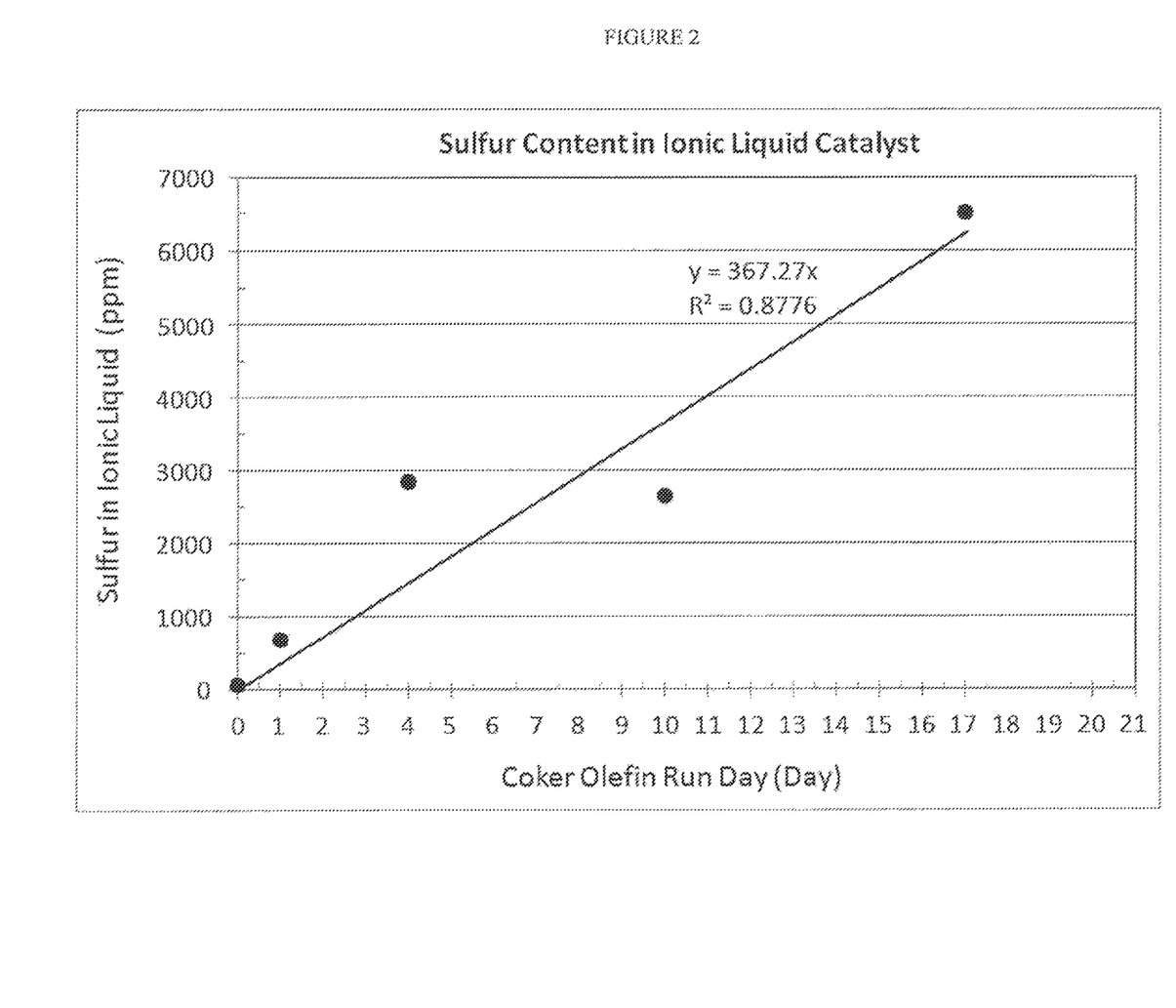
FIG. 2 is a chart showing the sulfur content in the ionic liquid catalyst during the alkylation examples described herein.

We observed build-up of sulfur content in the ionic liquid catalyst, as shown in FIG. 2. The sulfur content of the ionic liquid catalyst reached about 7,000 ppm by the 17th day, and the ionic liquid catalyst performance for the alkylation reaction was not affected at all. The final boiling points and yields of the alkylate gasoline blending components were not adversely affected by the increase in the sulfur in the ionic liquid catalyst. We expect that the ionic liquid catalyst can further accumulate sulfur contaminants without affecting its performance.

During the 17 days of operation, the regeneration unit temperature was maintained at about 177° C. (350° F.) and unit did not show any signs of degradation in regeneration performance. The $H_2S$ content in the off-gas from the regeneration reactor was measured using Draeger hydrogen sulfide ($H_2S$) detector tubes (Dräger-tubes®) by colorimetric gas detection and a Draeger tube pump. Dräger-tubes® is a registered trademark of Drägerwerk AG & Co. The $H_2S$ content was measured consistently from 250 to 350 ppm in the offgas. The constant detection of $H_2S$ from the offgas indicated some conversion of sulfur species in the ionic liquid catalyst during the regeneration process.

In order to alkylate pure coker LPG olefins to produce alkylate product with desirable properties, a catalyst especially resistant to impurities was needed. We surprisingly found that our ionic liquid catalyst was highly active and was able to produce quality alkylate with pure coker LPG as the olefin feed source for extended time periods while capturing the feed sulfur in the ionic liquid catalyst. This capability was beyond what conventional alkylation processes are capable of and we were surprised with its robustness.

While we do not want to be bound by theory, it appears that rapid oligomerization of diene is not extensive with the ionic liquid catalyst, and formation of heavy components can be suppressed. This is very different from the $H_2SO_4$ alkylation case shown in Example 5.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

The invention illustratively disclosed herein suitably may be practiced in the absence of any element which is not specifically disclosed herein.

It is claimed:

1. A process for making an alkylate gasoline blending component, comprising:
   a. providing an olefin feed comprising a sulfur contaminant;
   b. drying the olefin feed comprising the sulfur contaminant with a promoted alumina-based selective adsorbent that is customized to provide adsorption for polar organic compounds to produce a dried olefin feed comprising from 100 to 1000 wppm of a sulfur contaminant comprising mercaptans, alkyl sulfides including methyl tert-butyl sulfide, and alkyl disulfides, wherein methyl tert-butyl sulfide is formed during treatment with the selective adsorbent;
   c. feeding the dried olefin feed to a chloroaluminate ionic liquid catalyst, wherein a level of the sulfur contaminant accumulates in the chloroaluminate ionic liquid catalyst to make a sulfur-contaminated ionic liquid catalyst comprising 300 to 20,000 wppm of sulfur; and
   d. alkylating the dried olefin feed with an isoparaffin using the sulfur-contaminated ionic liquid catalyst to produce an alkylate gasoline blending component, wherein the alkylate gasoline blending component has a final boiling point below 221° C. (430° F.).

2. The process of claim 1, wherein the olefin feed comprises $C_3$ and $C_4$ olefins.

3. The process of claim 1, wherein the olefin feed comprising the sulfur contaminant comes from a refinery and comprises at least 20 wt % $C_3$ and $C_4$ olefins.

4. The process of claim 1, wherein the selective adsorbent changed sulfur species in the olefin feed.

5. The process of claim 1, wherein the olefin feed comprising the sulfur contaminant is a coker LPG stream comprising:

| Components | Wt % |
|---|---|
| Propane (C3) | 10.0-25.0 |
| Propene (C3=) | 4.0-8.0 |
| Isobutane (iC4) | 6.0-12.0 |
| n-Butane (nC4) | 25.0-40.0 |
| 1-Butene (1-C4=) | 8.0-11.0 |
| 2-Methylpropene (iC4=) | 5.0-10.0 |
| trans-2-Butene (t-2-C4=) | 3.0-7.0 |
| Cis-2-Butene (c-2-C4=) | 2.0-5.0 |
| 1-3-Butadiene (1-3-C4DE) | 0.0-1.0 |
| Isopentane (iC5) | 0.5-5.0 |
| n-Pentane (nC5) | 0.0-1.0 |
| C5+ | 1.1-3.0 |
| Total | 100.0 |
| Total C3= | 4.0-12.0 |
| Total C4= | 18.0-30.0 |
| Total Olefins | 22.0-42.0. |

6. The process of claim 1, wherein the chloroaluminate ionic liquid catalyst comprises an ammonium or a phosphonium cation.

7. The process of claim 1, wherein the alkylating is performed continuously for one to 365 days.

8. The process of claim 1, wherein the final boiling point is from 191 to 207° C. (376 to 404° F.).

9. The process of claim 1, wherein the isoparaffin comprises isobutane.

10. The process of claim 1, additionally comprising continuously sending a portion of the sulfur-contaminated ionic liquid catalyst to a regeneration reactor to regenerate the sulfur-contaminated ionic liquid catalyst and to maintain 0.5 to 10 wt % of a conjunct polymer in the sulfur-contaminated ionic liquid catalyst during the alkylating.

11. The process of claim 1, wherein the olefin feed is a coker LPG olefin that is not mixed with any other sources of olefins.

12. The process of claim 1, wherein the olefin feed is fed directly from a refinery process unit that produces the olefin feed, without any additional steps to further reduce an amount of the sulfur contaminant in the olefin feed.

13. The process of claim 1, wherein the olefin feed consists of coker LPG olefins.

14. A process to make an alkylate gasoline blending component, comprising:
   a. treating a coker LPG stream, containing coker LPG olefins, with an amine treater, a caustic treater, or a combination thereof, to produce a treated coker LPG stream having a total sulfur content from 100 to less than 500 wppm and a total mercaptans content from 10 to 150 wppm;
   b. drying the treated coker LPG stream with a promoted alumina-based selective adsorbent that is customized to provide adsorption for polar organic compounds to produce a dried coker LPG stream having from zero to less than 1 wppm water, from zero to 20 wppm total mercaptans, greater than 100 wppm total sulfur including methyl tert-butyl sulfide, and from zero to less than 100 wppm total oxygenates, wherein methyl tert-butyl sulfide is formed during treatment with the selective adsorbent;
   c. feeding the dried coker LPG stream, unmixed with any other olefins, and a refinery isobutane stream to an alkylation reactor containing an ionic liquid catalyst, wherein the ionic liquid catalyst becomes a sulfur-contaminated ionic liquid catalyst; and
   d. alkylating the olefins with an isobutane from the refinery isobutane stream using the sulfur-contaminated ionic liquid catalyst to produce an alkylate gasoline blending component, wherein the alkylate gasoline blending component has a final boiling point below 221° C. (430° F.).

15. The process of claim 14, wherein the coker LPG stream comprises at least 20 wt % $C_3$ and $C_4$ olefins.

16. The process of claim 14, wherein the coker LPG stream comprises:

| Components | Wt % |
|---|---|
| Propane (C3) | 10.0-25.0 |
| Propene (C3=) | 4.0-8.0 |
| Isobutane (iC4) | 6.0-12.0 |
| n-Butane (nC4) | 25.0-40.0 |
| 1-Butene (1-C4=) | 8.0-11.0 |
| 2-Methylpropene (iC4=) | 5.0-10.0 |
| trans-2-Butene (t-2-C4=) | 3.0-7.0 |
| Cis-2-Butene (c-2-C4=) | 2.0-5.0 |
| 1-3-Butadiene (1-3-C4DE) | 0.0-1.0 |
| Isopentane (iC5) | 0.5-5.0 |

-continued

| Components | Wt % |
|---|---|
| n-Pentane (nC5) | 0.0-1.0 |
| C5+ | 1.1-3.0 |
| Total | 100.0 |
| Total C3= | 4.0-12.0 |
| Total C4= | 18.0-30.0 |
| Total Coker LPG Olefins | 22.0-42.0. |

17. The process of claim 14, additionally comprising installing an ionic liquid alkylation reactor to perform the alkylating in an existing HF or $H_2SO_4$ refinery alkylation unit.

18. The process of claim 14, wherein the dried coker LPG stream comprises mercaptans, alkyl sulfides including the methyl tert-butyl sulfide, and alkyl disulfides.

19. The process of claim 14, wherein the promoted alumina-based selective adsorbent is smooth and spherical.

* * * * *